United States Patent
Taylor et al.

(10) Patent No.: US 6,471,976 B1
(45) Date of Patent: Oct. 29, 2002

(54) COPPER COMPLEX BACTERICIDE/FUNGICIDE AND METHOD OF MAKING SAME

(76) Inventors: Evelyn J. Taylor, Griffin Corporation, P.O. Box 1847, Valdosta, GA (US) 31603-1847; Mark A. Crawford, Griffin Corporation, P.O. Box 1847, Valdosta, GA (US) 31603-1847

(*) Notice: Subject to any disclaimer, the term of this patent is extended or adjusted under 35 U.S.C. 154(b) by 0 days.

(21) Appl. No.: 08/387,397

(22) Filed: Feb. 13, 1995

Related U.S. Application Data

(63) Continuation of application No. 08/013,158, filed on Feb. 1, 1993, now abandoned, which is a continuation of application No. 07/863,217, filed on Apr. 3, 1992, now abandoned, and a continuation-in-part of application No. 07/591,288, filed on Oct. 1, 1990.

(51) Int. Cl.[7] ............ A61K 31/44; A61K 9/64; A61K 9/62; A01N 25/08
(52) U.S. Cl. ............ 424/409; 424/409; 424/460; 424/463; 424/78.08
(58) Field of Search ............... 424/404, 405, 424/409, 630, 633, 78.08

(56) References Cited

U.S. PATENT DOCUMENTS

RE24,324 E   5/1957   Furness (List continued on next page.)

FOREIGN PATENT DOCUMENTS

| DE | 19005524  | 1/1969  |
|----|-----------|---------|
| EP | 0 039 788 | 10/1981 |
| EP | 0 039 788 | 11/1981 |
| EP | 0 237 946 | 3/1987  |
| EP | 0 480 614 | 10/1991 |
| FR | 914962    | 7/1946  |
| FR | 916489    | 8/1946  |
| FR | 943010    | 9/1948  |
| FR | 966315    | 3/1950  |
| FR | 2 255 017 | 7/1975  |
| FR | 2 417 943 | 9/1979  |
| FR | 2 668 031 | 4/1992  |
| GB | 493148    | 3/1938  |
| GB | 880270    | 4/1960  |
| GB | 880270    | 10/1961 |
| GB | 994830    | 6/1965  |
| GB | 2 077 740 | 4/1984  |

OTHER PUBLICATIONS

C.A. 115 (1):3 161g R. Tochikawa.*
N. Yamamori et al., "Application of Polymers Containing Copper Salts to Antifouling Paint".
A. Kondo, "Microcapsule Processing and Technology," 1979.
Copies of two Cassis searches.
M. Mandel, "Charge Interactions and Association in Polyelectrolyte Solutions. I. Some General Remarks".
V. Crescenzi et al., "Thermodynamics of Polycarboxylate Aqueous Solutions. I. Dilatometry and Calorimetry of Protonation and Coopper (11) Binding".
M. Morcellet, "Microcalorimetric Investigation of the Association of Syndiotactic Poly(Methacrylic Acid) with some Divalent Metal Ions".

(List continued on next page.)

Primary Examiner—Thurman K. Page
Assistant Examiner—S. Tran

(57) ABSTRACT

There is disclosed an improved copper complex bactericide/fungicide and a method of making and using the same. The improved bactericide/fungicide is prepared by forming an aqueous solution of a partially neutralized, water-soluble polycarboxylic acid having a molecular weight of between approximately 1,000 and 300,000 and a pH of between approximately 3 and 9. To this aqueous solution is added a copper-containing compound which when combined with said aqueous solution releases copper (II) ions which will form a water-soluble complex with said partially neutralized polycarboxylic acid. The water-soluble copper complex is applied to plants to prevent or inhibit bacterial and fungal disease growth thereon.

22 Claims, 6 Drawing Sheets

Effect of polyacrylic acid pH and copper source on copper concentration.

U.S. PATENT DOCUMENTS

| | | | |
|---|---|---|---|
| 3,428,731 A | | 2/1969 | Furness |
| 3,462,527 A | | 8/1969 | Tanabe et al. |
| 3,954,967 A | * | 5/1976 | Urton .................... 514/531 |
| 4,003,994 A | | 1/1977 | Downer et al. |
| 4,048,324 A | | 9/1977 | Kohn .................... 424/294 |
| 4,193,993 A | * | 3/1980 | Hilditch ................ 424/635 |
| 4,227,911 A | | 10/1980 | Leonard et al. ............ 71/77 |
| 4,244,836 A | | 1/1981 | Frensch et al. |
| 4,339,448 A | | 7/1982 | Dockner et al. |
| 4,409,358 A | | 10/1983 | Kraft et al. ............ 524/547 |
| 4,418,056 A | | 11/1983 | Gonzalez |
| 4,528,185 A | | 7/1985 | Kraft et al. ............ 424/81 |
| 4,677,143 A | * | 6/1987 | Laurin et al. ........... 424/635 |
| 4,732,762 A | | 3/1988 | Sjogren |
| 4,770,694 A | * | 9/1988 | Iwasaki .................. 71/93 |
| 4,851,557 A | * | 7/1989 | Kleemann et al. ......... 556/110 |
| 4,923,866 A | * | 5/1990 | Albert et al. ............ 514/483 |
| 5,004,760 A | * | 4/1991 | Patton et al. ........... 424/78.27 |
| 5,242,685 A | | 9/1993 | Ruppersberger et al. . 424/78.26 |
| 5,298,253 A | * | 3/1994 | LeFiles et al. ........... 424/409 |

OTHER PUBLICATIONS

C. Travers, et al. "The Complexing of Ca(II), Co(II), and Zn(II) by Polymetharcylic and Polyacrylic Acid".

R. Subramanian, X–ray Studies on Interpolymer Adducts Formed between Poly(N–vinylpyrrolidone and Poly(acylic acid)s.

H. Yokoi, "Interaction Modes between Heavy Metal Ions and Water–Soluble Polymers. 1. Spectroscopic and Magnetic Reexamination of the Aqueous Solutions of Cupric Ions and Poly(vinyl alcohol)".

M. Mandel, "Interaction of Polymethacrylic Acid and Bivalent Counterions".

M. Mandel, "Interaction of Poly(methacrylic Acid) and Biavalent Counterions".

S. Paoletti, et al. "Thermodynamics of Polycarboxylate Aqueous Solutions 3. Binding of Divalent Ions".

F. Yamashita, "Study of Metal–Polycarboxylate Complexes Employing Ion–Selective Electrodes Cu(II) and Cd(II) Compexes with Poly(acylic acid) and Poly(itaconic acid)".

S. Paoletti, "A Spectroscopic Investigation of Complexes of Divalent Metal Ions with Maleic Acid Copolymers".

W. Anapach, "Complexing of Nickel(II) and Cobalt(II) by a Polymethacrylic Acid Gel and Its Linear Polyelectrolyte Analog".

S. Noji, "Electron Spin Resonance Study of Poly(a–L–glutamic acid) and Poly(acrylic acid) Copper(II) Complexes in the Frozen State with Emphasis on the Complex Species".

S. Inoue, Polarographic Investigation of Biopolymers. III. Comparison between Poly(acrylic acid) and Poly(a, L–glutamic acid) as Regards the Complexing Behavior toward the Copper(II) Cadmium(II), and Nickel(II) Ions in the pH Range 3–7.

S. Fang, "Ionic Conductivity of Polyacid–Poly(Vinyl Alchohol)–Metal Ion Complex Membranes".

S. Das, "Photochemistry of Copper(II)–Poly(acrylic acid-)Complexes: Photogeneration and Photolysis of an Alkyl–Copper Intermediate".

S. Krupin, "Metal–Polymer Complexes Bases on Hydrolyzed Polyacrylonitrile".

P. McCluskey, "Infrared Spectral Studies of Various Metal Polyacrylates".

H. Nishide, "Complexation of Poly(acrylic acid)s with Uranyl Ion".

G. Manzini, "Copper(II) Binding by Natural Ionic Polysaccharides. Part I. Potentiometric and Spectroscopic Data".

S. Chatterjee, "Study of multicomponent complexes between polycarboxylic acid, transition metal ions and non–ionic polymers".

H. Gregor, "Metal–Polyelectrolyte Complexes. II. Complexes of Copper with Cross–Lined Polyacrylic and Polymethacrylic Acids".

E. Loebl, "Metal–Polyelectrolyte".

Chem. Abstract 115: 3161g.

Chem. Abstract 94: 11630.

Chem. Abstract 91: 75843q.

W. Anspach, "Complexing of Nickel(II) and Cobalt(II) by a Polymethacrylic Acid Gel and Its Linear Polyelectrolyte Analog".

E. Loebl, L.B. Luttinger and H.P. Gregor, "Metal–Polelectrolyte Complexes. III. Entropy and Enthalpy of Complexation for Polyacrylic Acid–Copper System" 1995.

H. Morawetz, The Nature of Copper (II) Compexes with Poly (Acrylic Acid) and Poly (Methacrylic Acid) May 1955.

R. Subramanian and P. Natarajan, Interaction between Poly (N–Vinylpyrrolidone) and Poly(acrylic Acid)s: Influence of Hydrogen and Cupriic Ions on the Adduct Formation, Journal of Polymer Science, Polymer Chemistry Ed., vol. 22, 437–451 (1984).

D.V.Subotic, J. Ferguson and B.C.H. Warren, "Turbidimetric Study of the Influence of $Cu^{2+}$ on the Kinetics of Complexation of Poly(Acrylic Acid) with Polyvinylpyrrolidone", Eur. Polym. J. vol. 2, No. 1, pp 61–64, 1991.

N.M. Kabanov; Kozhevnikova, "Reactions of the formation of ternary polymer–metal complexe," 1979.

N.M. Kabanov; A. M. Khvan, "Reactions of the formation of ternary polymer–metal complexe," 1979.

A.N. Bov, P. Vasil'ev, "Study of polymeric metallic complexes of polyacrylic and . . . ," 1980.

G.M. Zhaimina, Bimendina, "Viscometric studyof complexes of copy (II) ions with . . . ," 1983.

I.I. Sidorchuk, E. Amanov, "Study of the stability of complexes of polymeric ligands wit . . . ," 1983.

G.M. Zhaimina, Kudaibergen, "Study of Poly(acrylic acid)–copper (2+) interaction in aqueou . . . ," 1986.

E.G. Tropsha, A. Polinskii, "Formation of Complexes between poly(acrylic acid) and copper," 1986.

M.L. Brenerman, Barabanov, "Interaction of copper (2+) and manganese (2+) with poly(acryli . . . ," 1988.

O.A. Politova, S. Petrov, "Polarographic study of interaction of polyelectrolytes with . . . ," 1988.

V.Z. Annenkova, Gruznykh, "Structural study of mixed salts of polyacrylic acid . . . ," 1990.

G. Geuskens, A. DePauw and C. David, "Etude Cinetique de la Formation de Chelates des Acides Polyacryliques Iso– et Syndiotactique avec les ions $Cu^{2+}$", Eur. Polymer J. 1969, vol. 5, pp. 125–132.

Pierre Monjol, "Conportement polyelectrolytique des acides polyacryliques stereoreguliers. II. Influence de la stereoregularite sur l'association de l'acide polyacrylique avec l'ion $Cu^{2+}$," 1971.

Dialog Searches (2).

STN International Search (1).

Lexpat Search (1).

\* cited by examiner

Fig. 1 Effect of polyacrylic acid pH and copper source on copper concentration.

Fig. 2 Copper concentration vs. pH for different molecular weight polyacrylic acids Fig. 3 Copper concentration vs. polymer concentration for different MW polyacrylic acids Fig. 4 Copper concentration vs. pH for three polycarboxylate polymers Fig. 5 Copper concentration vs. pH for polyacrylic acid neutralized with different bases.

Colony diameter of Alternaria solani on CYE agar containing 3 forms of copper ed to produce
COPPER COMPLEX BACTERICIDE/FUNGICIDE AND METHOD OF MAKING SAME

CROSS-REFERENCE TO RELATED APPLICATIONS

This is a continuation of application Ser. No. 08/013,158, filed Feb. 1, 1993, now abandoned which is a continuation of application Ser. No. 07/863,217, filed Apr. 3, 1992, now abandoned and this application is a continuation-in-part of application Ser. No. 07/591,288 filed Oct. 1, 1990.

FIELD OF INVENTION

The present invention relates generally to bactericides and fungicides, and, more specifically, to a bactericide/fungicide which is based upon a complex of copper and a partially neutralized polycarboxylic acid.

BACKGROUND OF THE INVENTION

Bactericides/fungicides are known in the art as agents used to protect agricultural crops from damage caused by pathogenic bacteria/fungi. The use of such products is necessitated by the great losses caused by such organisms. To be economical, the cost of controlling plant diseases by the application of a bactericide/fungicide product must be offset by increased crop yield and quality.

Agricultural bactericides/fungicides are available in different types of formulations including wettable powders, emulsifiable concentrates, water-based flowables, and dry flowables (also known as water dispersible granules). Dry flowable products are generally dustless, free-flowing, granular products. Dry flowable formulations have recently gained in popularity among users because they offer advantages such as improved shelf life, substantially no dusting, easy pouring, a higher percentage of active ingredient, and more convenient packaging than other formulation types.

Copper based bactericides/fungicides are used extensively in agriculture. Several dry flowable copper based bactericides/fungicides are known in the art, these being: "Kocide DF" available from Griffin Corporation of Valdosta, Ga.; "Blueshield DF" and "Nu-Cop WDG" available from Micro Flo Company of Lakeland, Fla.; and "Sandoz COC DF" and "Sandoz $Cu_2O$ DF" available from Sandoz Ltd. of Switzerland.

Cupric hydroxide by itself is unstable. However, it is known in the art that cupric hydroxide can be stabilized by a phosphate process. U.S. Pat. No. Re. 24,324 (the disclosure of which is incorporated herein by reference) relates to a method of making stable cupric hydroxide. U.S. Pat. No. 3,428,731 (the disclosure of which is also incorporated herein by reference) relates to dispersions of phosphate stabilized cupric hydroxide. That patent discloses that aqueous dispersions of finely divided phosphate-process cupric hydroxide can be prepared by carefully regulating the pH of the dispersion and the calcium hardness of the aqueous vehicle. The patent also discloses that approximately 1% to 3% by weight of a dispersant should be added to the aqueous vehicle before the phosphate-process cupric hydroxide is added. Suitable dispersing agents are disclosed as including sodium lignosulfonate, the sodium salt of a polymeric carboxylic acid, sulfonated naphthalene, technical protein colloid, tallow dimethyl benzyl ammonium chloride, the sodium salt of polymerized alkyl aryl sulfonic acid, diethanolamide of a special fraction of coconut fatty acids, the sodium salt of condensed mono-naphthalene sulfonic acid and isooctyl phenyl polyethoxy ethanol.

The prior art copper based bactericide/fungicide products require the use of relatively large amounts of copper to effectively control disease. This relatively high level of copper detracts from cost effectiveness, contributes to soil residue problems and raises the potential for phytotoxicity. In addition, the methods used to produce these prior art products are not always cost effective.

Complexes of copper (II) ions with partially neutralized polyacrylic acid and with partially neutralized polymethacrylic acid in aqueous media are known. See for example F. Wall and S. Gill, "Interaction of Cupric Ions with Polyacrylic Acid," J. Phys. Chem., Vol. 58, page 1128 (1954); A. Kotliar and H. Morawetz, "Chelation of Copper (II) with Polyacrylic and Polymethacrylic Acid," J. American Chem. Soc., Vol. 77, page 3692 (1955). Heretofore, complexes of copper with partially neutralized polycarboxylic acids have not been known to possess bactericidal or fungicidal properties. In particular, such complexes were not previously known to be an effective bactericide or fungicide for agricultural use; yet, also be substantially nonphytotoxic. Furthermore, such complexes were not previously known to be effective bactericides or fungicides against copper tolerant bacteria.

Therefore, a need exists for a copper-based bactericide/fungicide formulation which provides biological activity, particularly against copper tolerant bacteria, with substantially no phytotoxicity.

SUMMARY OF THE INVENTION

The present invention satisfies the above-described needs by providing an improved bactericide/fungicide and an improved method of making and using the same. The improved bactericide/fungicide of the present invention is prepared by forming an aqueous solution of a partially neutralized, water-soluble polycarboxylic acid having a molecular weight of between approximately 1,000 and 300,000 and a pH of between approximately 3 and 9. To this aqueous solution is added a copper-containing compound which when combined with said aqueous solution releases copper (II) ions which will form a water-soluble complex with said partially neutralized polycarboxylic acid.

The bactericide/fungicide of the present invention is used to control bacterial/fungal diseases in plants by applying to plants a bactericide/fungicide consisting essentially of a complex of copper and a partially neutralized, water-soluble polycarboxylic acid having a molecular weight of between approximately 1,000 and 300,000 and a pH of between approximately 3 and 9.

Accordingly, it is an object of the present invention to provide an improved bactericide/fungicide and an improved method of making and using the same.

Another object of the present invention is to provide a bactericide/fungicide which is substantially nonphytotoxic to the plants to which it is applied.

A further object of the present invention is to provide a bactericide/fungicide which can be made from a variety of different copper sources.

Yet another object of the present invention is to provide a bactericide/fungicide which can be used to control copper tolerant bacteria.

Another object of the present invention is to provide a bactericide/fungicide which can be used on plants and crops which are injured by conventional copper-based bactericides/fungicides when used at optimum rates for disease control.

Still another object of the present invention is to provide a bactericide/fungicide which is substantially water-soluble so that it can be relatively easily removed from crops or plants to which it is applied so that it can be applied to crops later in the growing cycle and/or post-harvest.

Another object of the present invention is to provide a bactericide/fungicide which does not leave a colored residue on the crops or plants to which it is applied.

A further object of the present invention is to provide a bactericide/fungicide which is useful in foliar applications for disease control.

Still another object of the present invention is to provide a bactericide/fungicide which requires a lower copper use rate for the same level of protection which would be provided by copper hydroxide-based bactericides/fungicides.

A further object of the present invention is to provide a bactericide/fungicide which can be used to pretreat seed prior to planting.

Another object of the present invention is to provide a bactericide/fungicide which will control bacteria and/or fungi growth on substrates of various materials.

These and other objects, features and advantages of the present invention will become apparent after a review of the following detailed description of the disclosed embodiments and the appended drawing and claims.

DETAILED DESCRIPTION OF THE DISCLOSED EMBODIMENTS

Figure 1:
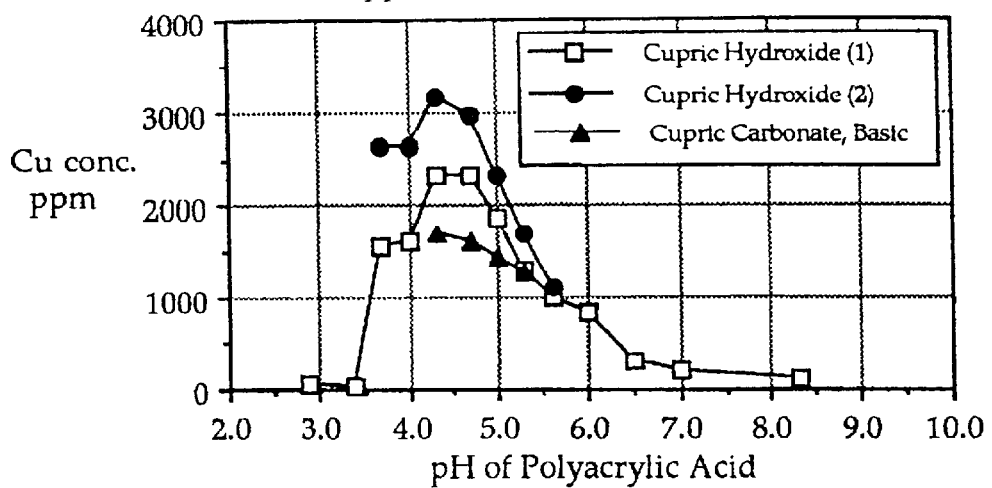
FIG. 1 is a graph of the concentration of copper plotted against the pH of neutralized polyacrylic acid at a concentration of 1% by weight (solids) for the three different sources of copper.

The present invention relates to an improved agricultural bactericide/fungicide formulation and to a method for producing a copper-based bactericide/fungicide. The novel product of the present invention offers improved biological activity over typical copper-based products, while requiring significantly less copper in its formulation. The decreased copper content reduces the bactericide/fungicide formulation's contribution to soil accumulation of copper. The bactericide/fungicide of the present invention is also substantially nonphytotoxic to the plants to which it is applied; particularly, in comparison to other water-soluble copper-based formulations.

A bactericide/fungicide formulation may be produced in accordance with the present invention by the following steps. An aqueous solution of a polycarboxylic acid is prepared by combining with water a water-soluble polycarboxylic acid. As used herein the term polycarboxylic acid shall mean both homopolymers and copolymers of carboxylic acids. The aqueous solution of the polycarboxylic acid is then partially neutralized with a basic material. To the aqueous solution of the water-soluble, partially neutralized polycarboxylic is added a copper-containing compound which when added to the aqueous solution releases copper (II) ions (or cupric ions) which will react with the partially neutralized polycarboxylic acid to form a complex therewith. The resulting copper complex will be substantially completely water-soluble.

As disclosed herein, the weights of the copper and the polycarboxylic acid components are stated as percent by weight in aqueous solution (unless specifically stated otherwise). The bactericide/fungicide of the present invention can also be prepared as a dry composition by drying the composition after complexing in the aqueous solution. Obviously, when the water is removed from the aqueous solution of the copper complex, the percentages by weight of the copper and polycarboxylic acid will change. However, these changes can be easily calculated by those skilled in the art based upon the percentages by weight of the components in the aqueous solution.

Polycarboxylic acids which are useful in the present invention include water-soluble polycarboxylic acids having molecular weights of between approximately 1,000 and 300,000; preferably between approximately 2,000 and 50,000. The precise structure of the polycarboxylic acid is not critical to the present invention. Examples of polycarboxylic acids which are useful in the present invention include polyacrylic acid, polymethacrylic acid, copolymers of acrylic acid and acrylamide, copolymers of acrylic acid and methacrylamide, copolymers of acrylic acid and acrylate esters, copolymers of acrylic acid and methacrylic acid, copolymers of acrylic acid and methacrylate esters, copolymers of acrylic acid and maleic anhydride, carboxymethylcellulose, copolymers of maleic acid and butadiene, polymers of maleic acid and maleic anhydride, copolymers of maleic acid and acrylic acid, and copolymers of methyl vinyl ether and maleic anhydride.

Polycarboxylic acids which by themselves are not water-soluble can be made useful in the present invention by converting the water-insoluble polycarboxylic acid to a water-soluble salt of the polycarboxylic acid. The techniques by which such salts are prepared are well known in the art. Generally speaking, however, such salts are prepared by reacting the polycarboxylic acid with basic materials, such as, sodium hydroxide; potassium hydroxide; $NaHCO_3$; $Na_2CO_3$; $NH_4OH$; $R_4N^+$ $OH^-$ wherein R is either $CH_3$ or $C_2H_5$; primary amines, such as methyl, ethyl, n-propyl, isopropyl, t-butyl; secondary amines, such as dimethyl, diethyl, di-n-propyl and di-isopropyl; and tertiary amines, such as trimethyl, triethyl, and tri-n-propyl.

There is no particular upper limit for the concentration of the polycarboxylic acid in the aqueous solution. The polycarboxylic acid can be added to the water to form a solution thereof in amounts sufficient to react with the copper-containing compound and to form a complex therewith. However, as the concentration of the polycarboxylic acid increases, the viscosity of the solution also increases. This is particularly true of relatively high molecular weight polycarboxylic acids. Generally, it is not desirable for the viscosity of the aqueous solution to be too great to effectively mix with the copper-containing compound. Practically speaking, concentrations of the polycarboxylic acid useful in he present invention are between approximately 0.2% by weight and 80% by weight; preferably between approximately 0.75% by weight and 20% by weight.

When the polycarboxylic acid is combined with water to form a solution thereof, the solution will generally have an acidic pH. It is a critical aspect of the present invention that the polycarboxylic acid be partially neutralized with a basic material so that the pH of the solution is between approximately 3 and 9; preferably between approximately 3.5 and 5. Generally, it has been observed that the amount of copper which can be complexed with the partially neutralized polycarboxylic acid is dependent, at least in part, upon the pH of the aqueous solution of the partially neutralized polycarboxylic acid. The concentration of the copper in the complex reaches a maximum between the pHs listed above. Outside the range of pH of 3 to 9, the amount of copper which will complex with the partially neutralized polycarboxylic acid is not practically useful.

The nature of the basic material which is used to neutralize the polycarboxylic acid is not critical to the present invention. Suitable neutralizing agents include sodium hydroxide; potassium hydroxide; $NaHCO_3$; $Na_2CO_3$; $NH_4OH$, $R_4N^+$ $OH^-$ wherein R is either $CH_3$ or $C_2H_5$; primary amines, such as methyl, ethyl, n-propyl, isopropyl, t-butyl; secondary amines, such as dimethyl, diethyl, di-n-propyl and di-isopropyl; and tertiary amines, such as trimethyl, triethyl, and tri-n-propyl.

The resulting partially neutralized polycarboxylic acid is a combination of a copolymer of polycarboxylic acid and a polycarboxylic salt thereof, such as sodium polyacrylate. Suitable partially neutralized polycarboxylic acids are commercially available. Such commercially available products include "Goodrite K-752" available from B. F. Goodrich Co. of Cleveland, Ohio. "Goodrite K-752" is a polyacrylic acid, partial sodium salt in water having the formula $(C_3H_4O_2)_x$ $(C_3H_3NaO_2)_y$; and DP6-2696 and DISPEX N40 both salts of polymeric carboxylic acid in aqueous solution available from Allied Colloids, Inc. of Suffolk, Va.

The copper-containing compounds which are useful in the present invention are those compounds which when combined with the aqueous solution of the partially neutralized polycarboxylic acid will provide copper (II) ions which will complex with the partially neutralized polycarboxylic acid. Copper-containing compounds which are useful in the present invention include $Cu(OH)_2$, $CuSO_4$, $Cu(ClO_4)_2$, $Cu_2O$, $Cu(NO_3)_2$, $CuCl_2$, copper oxychloride, basic copper carbonate and tribasic copper sulfate. Copper oxychloride has the chemical formula $3Cu(OH)_2.CuCl_2$. Basic copper carbonate has the formula $Cu(OH)_2.CuCO_3$. Tribasic copper sulfate has the formula $3Cu(OH)_2.CuSO_4$.

The copper-containing compound can be either water-soluble, such as, $CuSO_4$, $Cu(ClO_4)_2$, $Cu(NO_3)_2$ and $CuCl_2$, or substantially water-insoluble, such as, $Cu(OH)_2$, $Cu_2O$, tribasic copper sulfate, basic copper carbonate and copper oxychloride. The water-insoluble copper-containing compounds heretofore were not known to form complexes.

Copper hydroxide compounds which are useful in the present invention include both cupric hydroxide technical (phosphate stabilized using the process disclosed in U.S. Pat. Nos. Re. 24,324 and 3,428,731 the disclosures of which are both incorporated herein by reference) and copper hydrate, a purer form of copper hydroxide. Other stabilized forms of copper hydroxide can also be used.

Copper-containing compounds useful in the present invention are commercially available. Such commercially available products include KOCIDE® cupric hydroxide, a phosphate stabilized cupric hydroxide formulation grade agricultural fungicide containing 88% copper hydroxide and 12% inerts available from Griffin Corporation of Valdosta, Ga. Methods of producing phosphate stabilized cupric hydroxide are also disclosed in U.S. Pat. Nos. 3,428,731 and Re. 24,324.

The amount of the copper-containing compound which is added to the aqueous solution of the partially neutralized polycarboxylic acid is that amount which will be useful in the final product as a bactericide/fungicide. Generally speaking, in making the bactericide/fungicide of the present invention, it is desirable to complex as much copper with the partially neutralized polycarboxylic acid as is possible. Factors which affect the amount of copper which can be complexed with the partially neutralized polycarboxylic acid are the pH of the aqueous solution of the partially neutralized polycarboxylic acid, molecular weight of the polycarboxylic acid, and the concentration of the partially neutralized polycarboxylic acid.

Generally, it has been observed that when there is an excess of the water-insoluble copper-containing compound which will react to complex with the polycarboxylic acid, the excess copper-containing compound will not dissolve in the aqueous solution. This may or may not be an undesirable situation. If solid water-insoluble copper-containing compound is not desired in the composition of the present invention, it can be separated from the liquid portion by conventional means, such as by filtration. An excess of water-soluble copper-containing compound will result in the presence of non-complexed copper ions in solution. Such non-complexed copper ions in solution may cause the solution to be phytotoxic. Therefore, when the source of copper to complex with the partially neutralized polycarboxylic acid is from a water-soluble copper-containing compound, the amount of such copper-containing compound which is used should be an amount sufficient to react with the polycarboxylic acid, but not an amount which will produce excessive non-complexed copper ions which will thereby render the solution phytotoxic.

Amounts of the copper from the copper-containing compound which are useful in the present invention are between approximately 0.1% by weight and 5% by weight (copper metal equivalent); preferably, between approximately 0.1% by weight and 3.2% by weight (copper metal equivalent).

The aqueous copper complex solution can be used to treat plants in its liquid form as produced by the above-described process or it can be optionally dried to provide solid, substantially dry products which can be redispersed in water to form aqueous solutions for spray application. The aqueous copper complex solution can be dried in conventional drying equipment, such as an oven drier or a spray drier, or by freeze drying techniques. For drying by spray drying, a spray dryer equipped with either a single fluid nozzle, a hydraulic nozzle or a rotating disk atomizer can be used. Such a spray drier would typically have an inlet temperature between approximately 350° F. and 480° F. and an outlet temperature between approximately 150° F. and 260° F. Spray drying equipment and techniques for spray drying dispersions and solutions are well known in the art. Similarly, freeze drying equipment and techniques for freeze drying dispersions and solutions are well known in the art. Using techniques well known in the art, the bactericide/fungicide of the present invention can be prepared in various forms, such as flakes, powders, granules, tablets and solutions.

The bactericide/fungicide of the present invention may be applied directly to the leaves of a plant to control bacterial/ fungal diseases. The bactericide/fungicide is applied in its liquid form as produced by the above-described process or by mixing the dried form with water to again form an aqueous solution and spraying the resulting solution onto the plants to be treated using conventional agricultural sprayers and spraying techniques well known in the art. The bactericide/fungicide of the present invention in liquid form is preferably diluted with water and applied to the leaves of plants by spraying (either aerial or ground) or by chemigation at a rate of between approximately 0.1 and 6 pounds per acre metallic copper equivalent in a volume of water of between approximately 1 and 800 gallons per acre.

The bactericide/fungicide of the present invention is useful for treating bacterial and fungal diseases on various plants including citrus, such as grapefruit, lemon, lime, orange, tangelo and tangerine; field crops, such as alfalfa, oats, peanuts, potatoes, sugar beets, wheat, and barley; small fruits, such as blackberry, cranberry, currant, gooseberry, raspberry and strawberry; tree crops, such as almond, apple, apricot, avocado, banana, cacao, cherry, coffee, filberts, mango, nectarine, olive, peach, pear, pecan, plum, prune and walnut; vegetables, such as beans, broccoli, brussel sprout, cabbage, cantaloupe, carrot, cauliflower, celery, collards, cucumber, eggplant, honeydew, muskmelon, onions, peas, peppers, pumpkin, squash, tomato and watermelon; vines, such as grape, hops and kiwi; miscellaneous, such as ginseng, live oak and sycamore and ornamentals, such as aralia, azalea, begonia, bulbs (Easter lily, tulip, gladiolus), carnation, chrysanthemum, cotoneaster, euonymus, India hawthorn, ivy, pachysandra, periwinkle, philodendron, pyracantha, rose and yucca (Adams-Needle).

The bactericide/fungicide of the present invention is useful for treating plants with bacterial or fungal diseases, such as melanose, scab, pink pitting, greasy spot, brown rot, phytophthora, citrus canker, xanthomonas and cerospora leaf spots, black leaf spot (alternaria), alternaria blight, botrytis blight, powdery mildew, xanthomonas leaf spot, anthracnose, pseudomonas leaf spot, septoria leaf spot, entomosporium leaf spot, volutella leaf blight, phomopsis stem blight, bacterial leaf spot, fire blight, black spot, leaf curl, coryneum blight (shot hole), blossom blight, pseudomonas blight, shuck and kernal rot (*Phytophthora cactorum*), zonate leafspot (*Cristulariella pyramidalis*), walnut blight, bacterial blight (halo and common), brown spot, black rot (xanthomonas), downy mildew, cercospora early blight, septoria late blight, angular leaf spot, phomopsis, purple blotch, bacterial speck, gray leaf mold, septoria leaf spot, dead bud (*Pseudomonas syringae*), *Erwinia herbicola, Pseudomonas fluorescens*, stem blight, ball moss, leptosphaerulina leaf spots, helminthosporium spot blotch, leaf spot, cane spot, fruit rot, blossom brown rot, bacterial blast (pseudomonas), European canker, crown or collar rot, sigatoka, black pitting, black pod, coffee berry disease (*Collectotrichum coffeanum*), leaf rust (*Hemileia vastatrix*), iron spot (*Cercospora coffeicola*), pink disease (*Corticium salmonicolor*) eastern filbert blight, and peacock spot.

Certain bacteria strains have become resistant to treatment by conventional copper-based bactericides. However, the bactericide/fungicide of the present invention is particularly well suited for controlling copper tolerant bacteria, such as, *Xanthomonas campestris* and *Pseudomonas syringae*.

Since the bactericide/fungicide of the present invention is water-soluble it can be applied to various plants or crops and then relatively easily removed by washing or spraying with water. Consequently, the bactericide/fungicide of the present invention may be applied to crops later in their growth cycle than would otherwise be possible with conventional bactericides/fungicides. Furthermore, the bactericide/fungicide of the present invention can also be used to treat post-harvest crops, such as oranges, citrus, cucumbers and apples, to provide a protective barrier which can be easily removed by washing.

The bactericide/fungicide of the present invention when applied to plants and then permitted to dry thereon does not leave a colored residue on the plants as do conventional copper-based bactericides/fungicides. Therefore, the bactericide/fungicide of the present invention can be used to treat nursery crops and greenhouse ornamentals.

The reduced phytotoxicity of the bactericide/fungicide of the present invention allows it to be used to treat copper sensitive plants and crops, such as peaches, pears, apples, and lettuce, which would otherwise be injured by conventional copper-based bactericides/fungicides when used at optimum rates for disease control.

The bactericide/fungicide of the present invention can also be used to pretreat seed prior to planting. The bactericide/fungicide can be applied to seed using conventional seed treatment equipment known in the art by spraying the bactericide/fungicide onto the seed and allowing the bactericide/fungicide to dry thereon, thereby providing a coating on the seed. Furthermore, the treated seed can be handled and planted in the conventional manner for seed which has been treated with known copper-based bactericides/fungicides. The bactericide/fungicide of the present invention is particularly useful in controlling seed-borne inoculum and preventing the infection of germinating seedlings. Although the bactericide/fungicide of the present invention is useful in treating seed generally, it is particularly useful in treating seed for crops, such as rice, wheat, cotton, soybeans, beans, corn, and peanuts.

Enhanced retention of the bactericide/fungicide of the present invention on plant surfaces after exposure to rain may be achieved by adding certain functional agents to the concentrated composition or to the spray solution. Such compounds which are useful in the present invention include, but are not limited to polyvinylpyrrolidone (PVP), polyoxyethylene, polyvinyl alcohol, and polyacrylamide. These compounds are known in the art as sticker compounds. The sticker compounds are added in an amount which provides the desired degree of rainfastness without unduly affecting the bactericidal/fungicidal properties of the copper complex solution. Generally, amounts of the sticker compound which are added to the copper complex solution and which are useful in the present invention are between 0.1% and 10% by weight.

It has been observed that the amount of copper which can be complexed with the partially neutralized polycarboxylic acid is related to the molecular weight of the polycarboxylic acid. Generally, the higher the molecular weight of the polycarboxylic acid, the more copper which can be complex therewith. As stated above, however, as the molecular weight of the polycarboxylic acid increases, so does the viscosity. Therefore, in selecting a polycarboxylic acid for use in the present invention, the competing factors of copper content and viscosity must be balance against each other.

It is specifically contemplated that the bactericide/fungicide of the present invention can also be used to treat substrates other than plants and crops. For example, the bactericide/fungicide of the present invention can be used to protect against bacterial and/or fungal growth in or on various non-living substrates, such as textiles, plastics, metals, glass, woods, papers, foams, concrete, stone, and the like. The bactericide/fungicide of the present invention can be applied to the surface of the substrate by methods well known in the art, such as, spraying, painting, dipping and the like. Furthermore, for appropriate materials, the bactericide/fungicide of the present invention can be impregnated in the substrate. The bactericide/fungicide of the present invention can be used to prevent bacterial and fungal growth in hospital or medical environments, such as on clothing, linens, carpeting, tile or linoleum floors, and plastic counter surfaces. For such applications, the copper complex of the present invention is applied at a rate sufficient to prevent or inhibit bacterial and/or fungal growth on the treated surface. The rate of application of the copper complex will vary depending upon the type of material to which it is applied and the conditions to which the substrate is subjected. Generally, the bactericide/fungicide of the present invention can be applied to substrates at a rate which will provide between approximately 1 and 1,000 mg of copper (metal equivalent) per square centimeter of substrate surface.

The following examples are illustrative of the present invention and are not intended to limit the scope of the invention as set forth in the appended claims.

EXAMPLE 1

An aqueous solution is prepared by combining 959 grams of water and 40 grams of Goodrite K-752 (a 63% solution in water of a polyacrylic acid, molecular weight 2,100) which is neutralized to pH 7 with 50% NaOH. The solution is mixed at ambient temperature to assure complete solution of the partially neutralized Goodrite K-752 in the water. To this solution is added 1.42 grams of $Cu(OH)_2$ (56.4% metallic copper). The mixture is stirred for between 12 to 24 hours to assure complete dissolution of the $Cu(OH)_2$. The resulting clear blue solution is analyzed for copper. The analysis reveals that the aqueous solution contains 800 ppm copper.

EXAMPLE 2

An aqueous solution of Goodrite K-752 at pH 4.5 is prepared by dissolving 113.4 grams of Goodrite K-752 in 433.8 grams of water and neutralizing with 21.4 grams of 50% NaOH. The partially neutralized Goodrite K-752 is added to 789 grams of water and stirred until the solution is homogeneous. To this solution is added 32.3 grams of copper hydrate (62% metallic copper). The mixture is stirred for between 12 to 24 hours to assure complete dissolution of the copper hydrate. The resulting clear blue solution contains 2% by weight copper metal equivalent.

EXAMPLE 3

An aqueous solution is prepared by combining 940 grams of deionized water and 60 grams of Goodrite K-752 (63% solution in water of a polyacrylic acid, molecular weight 2,100) which is neutralized with 50% sodium hydroxide to a pH of approximately 7. The solution is mixed at ambient temperature to assure complete solution of the Goodrite K-752 in the water. To the partially neutralized aqueous solution of Goodrite K-752 is added 10 grams of $Cu(OH)_2$. The aqueous dispersion is then mixed for a period of 24 to 48 hours to allow sufficient time for complete reaction of the copper hydroxide with the partially neutralized polyacrylic acid. Since the copper hydroxide is substantially water-insoluble, the excess undissolved copper hydroxide remains in solid form in the dispersion. The dispersion is then filtered to separate the liquid phase from the solid copper hydroxide using a 0.20 µm filter. The filtrate is then analyzed for copper. The analysis reveals that the aqueous solution contains 1270 ppm Cu (metal equivalent).

EXAMPLE 4

An aqueous solution is prepared by combining 989 grams of water and 10 grams of Goodrite K-752 (a 63% solution in water of a polyacrylic acid, molecular weight 2,100) which is neutralized with 50% sodium hydroxide to a pH of approximately 7. The solution is mixed at ambient temperature to assure complete solution of the Goodrite K-752 in the water. To the partially neutralized aqueous solution of Goodrite K-752 is added 1.0 grams of $CuSO_4$. The mixture is stirred for period of 30 minutes to assure complete solution of the copper sulfate. The solution is then analyzed for copper. The analysis reveals that the aqueous solution contains 800 ppm Cu (metal equivalent). The solution is tested for biological activity and demonstrates essentially no phytotoxicity similar to conventional aqueous dispersions of cupric hydroxide at an equal level of copper content. Equal levels of free ionic copper from copper sulfate result in severe plant injury and necrosis.

EXAMPLE 5

An aqueous solution is prepared by combining 1000 grams of water and 20 grams of Goodrite K-752 (a polyacrylic acid having a molecular weight of approximately 2,100). The solution is mixed at ambient temperature to assure complete solution of the Goodrite K-752 in the water. To this solution is added enough sodium hydroxide to partially neutralize the Goodrite K-752 to a pH of approximately 7. To the partially neutralized aqueous solution of Goodrite K-752 is added 2 grams of $CuCl_2$. The mixture is stirred for period of 30 minutes to assure complete solution of the cupric chloride. The solution is then analyzed for copper. The analysis reveals that the aqueous solution contains 1000 ppm Cu (metal equivalent).

EXAMPLE 6

An aqueous solution is prepared by combining 960 grams of water and 40 grams of Goodrite K-752 (a 63% solution in water of a polyacrylic acid, molecular weight 2,100) which is neutralized with 50% sodium hydroxide to a pH of approximately 7. The solution is mixed at ambient temperature to assure complete solution of the Goodrite K-752 in the water. To the partially neutralized aqueous solution of Goodrite K-752 is added 10 grams of copper oxychloride. The aqueous dispersion is mixed for a period of 24 to 48 hours to allow time for the copper to be complexed with the polymer. Since the copper oxychloride is substantially water-insoluble, the excess copper oxychloride substantially remains in solid form in the dispersion. The dispersion is then filtered to separate the liquid phase from the solid copper hydroxide using a 0.20 µm filter. The filtrate is then analyzed for copper. The analysis reveals that the aqueous solution contains 325 ppm Cu (metal equivalent).

EXAMPLE 7

A series of six samples containing 800 ppm copper (4× the estimated $LD_{90}$ rate of 200 ppm for the control of *Colletotrichum lagenarium* on cucumber plants) from copper sulfate are prepared. The copper is complexed in aqueous solutions of polycarboxylic acid (Goodrite K-752) partially neutralized to a pH of 7 with sodium hydroxide. The different samples contain the following concentrations of polymer: 4%, 2%, 1%, 0.75%, 0.5% and 0.25%. Samples containing 4%, 2% and 1% polymer give clear blue solutions, although the color becomes more green as the polymer content decreases. Below a polymer content of 0.75%, a blue-green precipitate forms, leaving a colorless upper layer. It is believed that an excess of copper causes the polymer to become insoluble, possibly through cross-linking. The samples containing from 4% to 0.75% polymer show substantially no phytotoxicity on greenhouse cucumbers with the samples containing 1% and 0.75% polymer showing the least amount of phytotoxicity. Those samples also show efficacy as bactericides/fungicides with respect to *Colletotrichum lagenarium* on cucumber plants. Cucumber plants treated with the same rate of free ionic copper from copper sulfate are severely injured and necrotic. Plants treated with copper sulfate can not be evaluated for efficacy due to severe injury.

EXAMPLE 8

Copper complexes of polycarboxylic acids are prepared in accordance with Examples 1 and 4 above using separately $CuSO_4$ and $Cu(OH)_2$ as the sources of copper. Samples of each copper source are prepared at concentrations of 800 ppm, 400 ppm, 200 ppm and 100 ppm copper (metal equivalent). A cumulative phytotoxicity test is conducted on tomato plants and pepper plants. Each sample is applied to the plants four times at weekly intervals. No phytotoxicity of any kind is observed

EXAMPLE 9

Copper complexes of polycarboxylic acids are prepared in accordance with Example 1 except the molecular weight of the polyacrylic acid as well as the pH of the partially neutralized polyacrylic acid are varied for different samples. Several samples of polyacrylic acid having different molecular weights are obtained from B. F. Goodrich. These samples are: Goodrite K-752 (molecular weight 2,100); Goodrite K-732 (molecular weight 5,100); Goodrite K-XP82 (molecular weight 2,800); and Goodrite K-XP83 (molecular weight 5,800). Aqueous solutions of the polymer are prepared; each solution containing 1.6% of polymer solids. The samples are neutralized with sodium hydroxide to the pHs shown below. Copper complexes are prepared from each of the neutralized samples using excess amounts of $Cu(OH)_2$. The samples are filtered through a 0.22 m syringe filter and analyzed for copper. The results are shown in the Table 1 below:

TABLE 1

| Polyacrylic Acid (PAA) | pH of NaPAA | pH of Filtered Complex Solution | Cu(ppm) |
| --- | --- | --- | --- |
| Goodrite K-752 | 5.0 | 6.9 | 2940 |
| Goodrite K-752 | 5.7 | 7.6 | 1320 |
| Goodrite K-752 | 6.7 | 9.2 | 503 |
| Goodrite K-752 | 7.0 | 9.5 | 500 |
| Goodrite K-752 | 7.6 | 9.9 | 770 |
| Goodrite K-732 | 5.0 | 7.0 | 3086 |
| Goodrite K-732 | 5.5 | 8.0 | 2840 |
| Goodrite K-732 | 6.0 | 8.6 | 1095 |
| Goodrite K-732 | 6.6 | 9.5 | 444 |
| Goodrite K-732 | 7.1 | 9.8 | 795 |
| Goodrite K-732 | 7.6 | 10.0 | 200 |
| Goodrite K-XP82 | 7.1 | 9.7 | 119 |
| Goodrite K-XP83 | 7.1 | 9.7 | 217 |

As can be seen from the Table 1, although there is considerable variation in the results, pH clearly has a much more significant effect on the amount of copper that can be complexed than does molecular weight in this range from 2,100 to 5,800.

Figure 2:
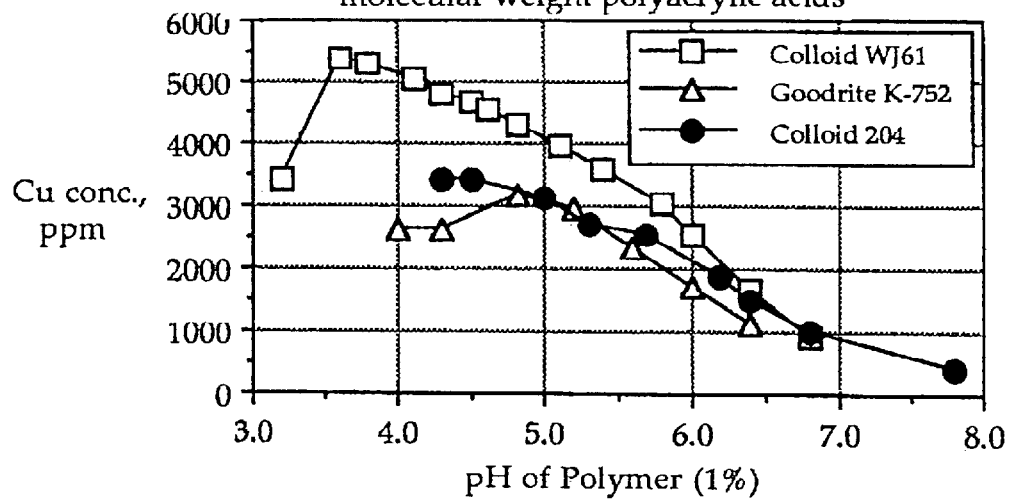
FIG. 2 is a graph of the concentration of copper plotted against the pH of neutralized polycarboxylic acids at a concentration of 1% by weight (solids) for the three different polycarboxylic acids.

Additional samples were prepared as described above using three different polymers and copper hydrate as the source of copper. The three polymers which were used were Goodrite K-752 (polyacrylic acid, molecular weight 2,100); Colloid WJ61 (polyacrylic acid, molecular weight 60,000) available from Rhone-Poulenc and Colloid 204 (polyacrylic acid, molecular weight 10,000) also available from Rhone-Poulenc. The results of this comparison are shown in FIG. 2 where the concentration of copper (metal equivalent) is plotted against the pH of the neutralized polymer at a concentration of 1% by weight of polyacrylic acid solids for the three different polymers. Again, as can be seen from FIG. 2, the dominating factor in the amount of copper complexed is the pH of the neutralized polymer, but the highest molecular weight polymer (Colloid WJ61) does complex significantly more copper than the other polymers in the pH range of 3.5 to 6.

Figure 3:
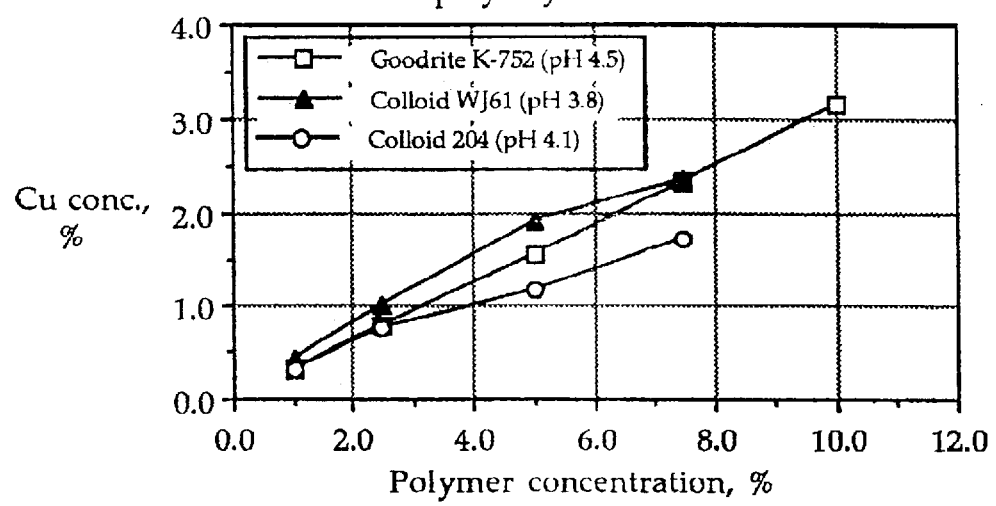
FIG. 3 is a graph of the concentration of copper plotted against the concentration of neutralized polycarboxylic acid (solids) for three different polycarboxylic acids.

Using the same copper complex solutions described above, the amount of complexed copper is measured for solutions in which the pH of the partially neutralized polycarboxylic acid is optimal for complexing copper and the amount of polymer is varied between 1% and 10% by weight of polyacrylic acid solids. The results of this test are shown in FIG. 3 wherein the amount of copper is graphed against the concentrations of the polymer for each of the three different polymers.

EXAMPLE 10

Copper complexes of polycarboxylic acid are prepared in accordance with Example 3 except the pH of the partially neutralized polyacrylic acid is varied for different samples. The complexes are formed by preparing aqueous solutions containing 1% by weight polymer solids of a polyacrylic acid (Goodrite K-752) which are partially neutralized using sodium hydroxide to pHs ranging from approximately 3 to approximately 8.5. Excess amounts of copper from three different copper sources are then added to the partially neutralized polymer solutions. One source is cupric hydroxide technical (phosphate stabilized using the process disclosed in U.S. Pat. Nos. Re. 24,324 and 3,428,731); another source is copper hydrate (a purer form of cupric hydroxide). The third source is basic cupric carbonate. The liquid portions of the samples are separated from the solid copper-containing compounds and the liquid portions are analyzed for copper. The results of the test are shown in FIG. 1 wherein the concentration of copper (metal equivalent in ppm) is plotted against pH of the neutralized polymer solutions for each of the various samples.

It can be seen from the graph that when cupric hydroxide technical is used as the source of copper, the maximum amount of copper which can be complexed occurs at a pH of approximately 4.5. However, when copper hydrate is used as the source of copper, the maximum copper complexation occurs at approximately the same pH, but approximately 35% more copper can be complexed using the same amount of polyacrylic acid. The impurities in the cupric hydroxide technical, most likely the residual salts, apparently affect the ability of the polymer to complex copper.

EXAMPLE 11

Copper complexes of polyacrylic acid are prepared from various sources of copper by adding the copper-containing compounds to aqueous solutions of 4% Goodrite K-752 partially neutralized to a pH of 7 using sodium hydroxide.

The samples are prepared in accordance with the procedures described in Examples 3 and 4 above depending upon whether the copper is water-soluble or water-insoluble. The sources of copper used to prepare the complexes are cupric chloride, copper oxychloride, cuprous oxide and basic copper carbonate. All of the sources of copper formed complexes with the partially neutralized polyacrylic acid.

EXAMPLE 12

A copper complex of polyacrylic acid is prepared by adding 1.5% copper (metal equivalent) from cupric hydroxide to an aqueous solution of 12% by weight polymer solids Goodrite K-752 partially neutralized to a pH of 4.8 using sodium hydroxide. The mixture is stirred for approximately 12 hours producing a clear, dark blue solution with no undissolved cupric hydroxide. The solution is then freeze dried using a Labconco lyophilizer at −50° C. under vacuum. The resulting product is a blue, honeycombed, crumbly solid which redissolves easily in water to give a blue-green solution. The dry product contains 8.57% copper and 5% water. An X-ray diffraction spectrum of the dry powder displays no peaks. This indicates that the dry copper complex does not have a crystalline structure.

EXAMPLE 13

Copper complexes of polyacrylic acids (obtained from Polysciences) having various molecular weights are prepared by adding excess amounts of copper from cupric hydroxide to a 1% by weight aqueous solution of the partially neutralized polymer at a pH of 5 (neutralized using sodium hydroxide). The liquid portion is separated from the solid cupric hydroxide by filtration and the liquid portion is analyzed for copper. Table 2 below lists the maximum copper complexed by these samples.

TABLE 2

| Molecular Weight | Cu Concentration (ppm) |
| --- | --- |
| 2,000 | 2330 |
| 5,000 | 2730 |
| 50,000 | 3500 |
| 90,000 | 3530 |
| 150,000 | 3200 |

EXAMPLE 14

Figure 4:
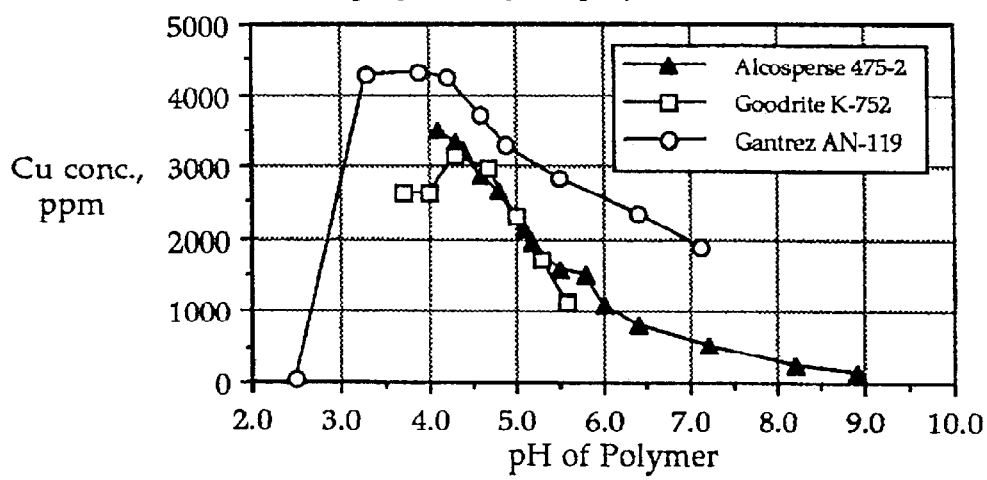
FIG. 4 is a graph of the concentration of copper plotted against the pH of neutralized polycarboxylic acid solutions for three different polycarboxylic acids.

Copper complexes of polycarboxylic acids prepared from three different polymers are prepared. The three polycarboxylic acids are Alcosperse 475-2, a 70/30 copolymer of acrylic acid and maleic acid and having a molecular weight of 20,000, available from Alco Chemical Corp.; Gantrez AN-119, a 50/50 copolymer of methyl vinyl ether and maleic anhydride and having a molecular weight of 20,000, available from GAF Corp.; and Goodrite K-752. The complexes are formed by preparing aqueous solutions containing 1% by weight polymer solids of a polyacrylic acid (Goodrite K-752) which are partially neutralized using sodium hydroxide to pHs ranging from approximately 2.5 to approximately 9. Excess cupric hydroxide is then added to the solutions of polymer. The liquid portion is separated from the undissolved solid cupric hydroxide by filtration and the liquid portion is analyzed for copper. The results of the test are shown in FIG. 4, wherein the concentration of the copper in the complexed product is graphed against the pH of the neutralized polymer solutions. The analysis reveals that all three polymers formed complexes with the copper. These copper complexes are biologically active against *Alternaria solani* and *Xanthomonas campestris* pv. *vescatoria*.

EXAMPLE 15

Copper complexes of polyacrylic acids are prepared according to Examples 3 and 4 above depending upon whether the source of copper is water-soluble or water-insoluble. The liquid portions of the copper complexes are then tested for efficacy against *Xanthomonas campestris* pv. *vescatoria*. Separate samples of casitone yeast extract (CYE) culture media are amended with the copper complexes to obtain metallic copper concentrations of 1, 2, 4, 6, 8, 10, 20, 40, 60, 80, and 100 ppm copper, respectively. All comparisons are made to copper sulfate at the same rates since this form of copper is known to be biologically active in agar media. Bacterial cultures produced in CYE media are streaked onto the agar and incubated for 5 days at 27° C. Control is based on the presence or absence of bacterial colonies. All copper complex samples and the copper sulfate samples control bacteria at 6 ppm and above. These tests demonstrate that the copper complex samples made in accordance with the present invention are as active as copper sulfate samples. The results of the test are shown further in Table 3 below.

TABLE 3

| Polycarboxylic Acid | Copper Source | $LD_{95}$ in CYE Agar, ppm Cu |
| --- | --- | --- |
| polyacrylic acid | cupric hydroxide | 6 |
| polyacrylic acid | copper sulfate | 6 |
| polyacrylic acid | $CU(ClO_4)_2$ | 6 |
| polyacrylic acid | $Cu_2O$ | 6 |
| polyacrylic acid | $CU(NO_3)_2$ | 6 |
| polyacrylic acid | $CUCl_2$ | 6 |
| polyacrylic acid | copper oxychloride | 6 |
| polyacrylic acid | tribasic copper sulfate | 6 |
| polyacrylic acid | basic copper carbonate | 6 |
| polyacrylic acid | copper hydrate | 6 |
| polymethacrylic acid | copper hydrate | 6 |
| copolymer of acrylic acid and acrylamide | cupric hydroxide | 6 |
| copolymer of acrylic acid and methacrylamide | cupric hydroxide | 6 |
| copolymer of acrylic acid and acrylate esters | cupric hydroxide | 6 |
| copolymer of acrylic acid and methacrylic acid | cupric hydroxide | 6 |
| copolymer of acrylic acid and methacrylate esters | cupric hydroxide | 6 |
| copolymer of acrylic acid and maieic anhydride | cupric hydroxide | 6 |
| carboxymethylcellulose | cupric hydroxide | 6 |
| copolymer of maleic acid and butadiene | cupric hydroxide | 6 |
| copolymer of maleic acid and maleic anhydride | cupric hydroxide | 6 |
| copolymer of maleic acid and acrylic acid | cupric hydroxide | 6 |
| copolymer of methyl vinyl ether and maleic anhydride | cupric hydroxide | 6 |
| none | copper sulfate | 6 |

EXAMPLE 16

Copper complexes of polyacrylic acids are formed according to the Examples listed in Table 4 below. The liquid portions of the copper complexes are then tested for efficacy against *Alternaria solani*. The copper complexes are tested in CYE culture media inoculated with the target fungi. Separate samples of culture media are amended with the copper complexes to obtain metallic copper concentrations of 1, 10, 20, 40, 60, 80, and 100 ppm copper, respectively. All comparisons are made to copper sulfate at the same rates since this form of copper is known to be biologically active in agar media. Actively growing cultures of *Alternaria solani* are sampled with a 7 mm cork borer around the outer circumference of the colony and placed in the center of culture dishes containing the copper amended media. These samples are incubated at 28° C. for 10 days. Radial culture diameters are measured to determine the effect of the copper on the growth of the fungi. The $LD_{90}$ of the copper complex samples is 100 ppm copper; whereas, the $LD_{90}$ for the copper sulfate is 80 ppm copper. These tests demonstrate that the copper complex samples made in accordance with the present invention are substantially as active as the copper sulfate samples. Results of the efficacy tests for various polycarboxylic acids and various sources of copper are reported in Table 4 below and in FIG. 6.

TABLE 4

| Conc. of PAA Solids | Molecular Weight PAA | pH of Partially Neutralized PAA | Copper Source | Example of Preparation | Copper Conc. in Complex Solution | $LD_{90}$ in CYE Agar, ppm Cu |
| --- | --- | --- | --- | --- | --- | --- |
| 2.50 | 2,100 | 7.0 | cupric hydroxide | 3 | 1270 ppm | 100 |
| 1.67* | 2,100 | 7.0 | cupric hydroxide | 1 | 800 ppm | 100 |
| 0.42* | 2,100 | 7.0 | cupric sulfate | 4 | 800 ppm | 100 |
| 6.67 | 2,100 | 5.3 | copper hydrate | 1 | 1.0% | 100 |
| 6.67 | 2,100 | 5.0 | copper hydrate | 1 | 1.0% | 100 |
| 0.64 | 2,100 | 4.8 | cupric hydroxide | 1 | 1000 ppm | 100 |
| 1.74 | 2,100 | 4.8 | cupric hydroxide | 1 | 2000 ppm | 100 |
| 1.30 | 2,100 | 4.8 | cupric hydroxide | 1 | 2000 ppm | 100 |
| 12.00** | 2,100 | 4.8 | cupric hydroxide | 12 | 1.5% | 100 |
| 1.20 | 2,100 | 7.0 | cupric chloride | 5 | 1030 ppm | 100 |
| 1.67 | 2,100 | 7.0 | copper oxychloride | 6 | 325 ppm | 100 |
| 7.14 | 2,100 | 4.5 | copper hydrate | 2 | 2.0% | 100 |
| 20.00 | 2,100 | 4.5 | copper hydrate | 1 | 3.5% | 100 |
| 1.00 | 5,000 | 5.2 | cupric hydroxide | 3 | 2730 ppm | 100 |
| 1.60 | 5,800 | 7.1 | cupric hydroxide | 3 | 220 ppm | 100 |
| 5.00 | 10,000 | 4.1 | copper hydrate | 3 | 1.2% | 100 |
| 1.00 | 50,000 | 5.0 | cupric hydroxide | 3 | 3500 ppm | 100 |
| 2.85 | 60,000 | 4.1 | copper hydrate | 1 | 1.0% | 100 |
| 1.00 | 90,000 | 5.0 | cupric hydroxide | 3 | 3530 ppm | 100 |
| 1.00 | 150,000 | 5.0 | cupric hydroxide | 3 | 3200 ppm | 100 |
| 1.00 | 240,000 | 5.0 | cupric hydroxide | 3 | 3150 ppm | 100 |
| None | | | cupric sulfate | | | 80 |

Figure 6:
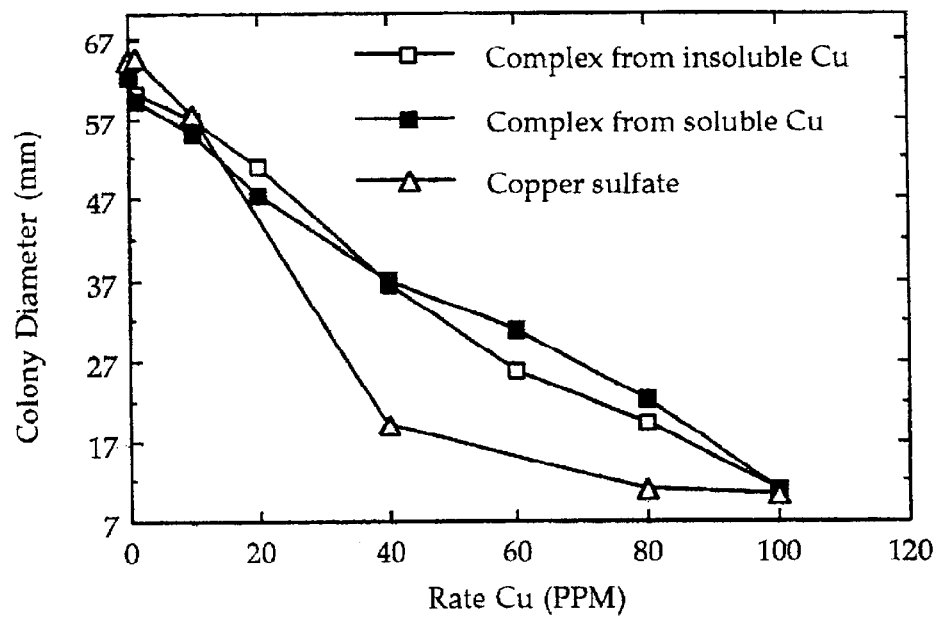
FIG. 6 is a graph of the colony diameter (mm) of *Alternaria solani* plotted against the copper concentration (ppm) for three different copper sources.

*Complexes used in test shown in FIG. 6.
**Both the copper complex solution and the freeze dried material containing 8.57% Cu prepared in Example 12 are tested.

EXAMPLE 17

Copper complexes of polyacrylic acids are prepared according to the Examples listed in Table 5 below. The liquid portions of the copper complexes are tested for efficacy against a strain of *Xanthomonas campestris* pv. *vescatoria* that is known to be resistant to conventional copper based bactericides/fungicides. Material prepared in accordance with Example 12 is dissolved in agar for testing. The copper complexes are tested in CYE agar inoculated with The copper complexes are tested in CYE agar inoculated with the target bacteria. Separate samples of culture media are amended with the copper complexes to obtain media samples containing metallic copper concentrations of 50, 100, 200, and 300 ppm copper, respectively. All comparisons are made to copper sulfate at the same rates since this form of copper is known to be biologically active in agar media. Bacterial cultures produced in CYE media amended with 25 ppm copper are streaked onto the agar and incubated for 5 days at 27° C. Control is based upon the presence or absence of bacterial colonies. Copper complex samples control copper tolerant bacteria at 300 ppm and copper sulfate controls bacteria at 100 ppm. Results of the efficacy tests are reported further in Table 5.

TABLE 5

| Conc. of PAA Solids | Molecular Weight of PAA | pH of Partially Neutralized PAA | Copper Source | Example of Preparation | Copper Conc. In Complex Solution | LD$_{90}$ in CYE agar, ppm Cu |
|---|---|---|---|---|---|---|
| 1.67 | 2,100 | 7.0 | cupric hydroxide | 1 | 800 ppm | 300 |
| 0.42 | 2,100 | 7.0 | cupric sulfate | 4 | 800 ppm | 300 |
| 6.67 | 2,100 | 5.3 | copper hydrate | 1 | 1.0% | 300 |
| 6.67 | 2,100 | 5.0 | copper hydrate | 1 | 1.0% | 300 |
| 12.00* | 2,100 | 4.8 | cupric hydroxide | 12 | 1.5% | 300 |
| 0.80 | 2,100 | 4.8 | copper hydrate | 1 | 2000 ppm | 300 |
| 1.06 | 2,100 | 4.8 | copper hydrate | 1 | 2000 ppm | 300 |
| 1.60 | 2,100 | 4.8 | copper hydrate | 1 | 2000 ppm | 300 |
| 3.75 | 2,100 | 4.5 | copper hydrate | 1 | 1.0% | 300 |
| 6.25 | 2,100 | 4.5 | copper hydrate | 1 | 1.0% | 300 |
| 8.00 | 2,100 | 4.5 | copper hydrate | 1 | 1.0% | 300 |
| 7.14 | 2,100 | 4.5 | copper hydrate | 2 | 2.0% | 300 |
| 20.00 | 2,100 | 4.5 | copper hydrate | 1 | 3.5% | 300 |
| 5.00 | 10,000 | 4.1 | copper hydrate | 3 | 1.2% | 300 |
| 2.50 | 60,000 | 3.8 | copper hydrate | 3 | 1.0% | 300 |
| None | — | — | cupric sulfate | — | — | 100 |

*Both the copper complex solution and the freeze dried material containing 8.57% Cu prepared in Example 12 are tested.

EXAMPLE 18

The copper complex solution prepared according to Example 2 is applied to wheat seed at 7, 14 and 28 grams Cu/cwt seed by spraying the seed using a laboratory seed treater. The treated seed is air-dried in trays prior to planting. Fifty seeds are sown in soil in flats to evaluate germination and growth after emergence. All treatments are compared to a conventional copper-based bactericide/fungicide (Kocide Seed Dressing) at 28 grams Cu/cwt. Germination and growth are similar for all treatments (see Table 6 below). No phytotoxicity of emerging seedlings is noted.

TABLE 6

| Treatment | g/cwt seed | % Germination |
|---|---|---|
| Kocide Seed Dressing | 28 | 47 |
| Example 2 | 7 | 48 |
| Example 2 | 14 | 48 |
| Example 2 | 28 | 48 |
| Untreated | 0 | 45 |

EXAMPLE 19

The copper complex solution prepared according to Example 2 is applied to oranges at 100, 500, and 1000 ppm by dipping the fruit into the respective solutions and allowing the solution to dry on fruit surface. Before the fruit are dipped, they are inoculated with *Alternaria citri, Phytophthora citrophthora, Penicillium digatatum* and *Colletotrichum gloeosporioides*. The fruit are stored at 5° C. and 80% relative humidity for 14 days after which the number of diseased fruit are counted. At the end of the test period, 100% of untreated fruit are diseased and 35%, 10%, and 8% of fruit treated with 100, 500 and 1000 ppm Cu are diseased respectively. No scaring or discoloration of the fruit is observed.

EXAMPLE 20

The copper complex solution prepared according to Example 2 is applied to geranium plants at 1000 ppm Cu, five times at weekly intervals. At the end of the test period, residues are evaluated and compared to conventional copper-based bactericides/fungicides applied at the same rate of copper. Compared to the conventional treatments, residues are not clearly visible with the naked eye. After residues are evaluated, plants are subjected to overhead irrigation. After the plants are dry, residues are again evaluated. Conventional fungicide treatment leaves a highly visible residue while plants treated with the copper complex have almost no trace of residue remaining. No phytotoxicity of any kind is observed.

EXAMPLE 21

The copper complex solution prepared according to Example 2 is applied to cotton burlap fabric. Separate samples of the fabric are treated by dipping the fabric in a 1000 ppm solution of the copper complex and in a solution of copper sulfate respectively. Another sample of the fabric is not treated at all. The fabric samples are then buried in nonsterile field soil for a period of 2 months. At the end of the test period, the untreated fabric is partially decomposed and those samples treated with copper complex and copper sulfate are substantially intact and undecomposed.

EXAMPLE 22

Figure 5:
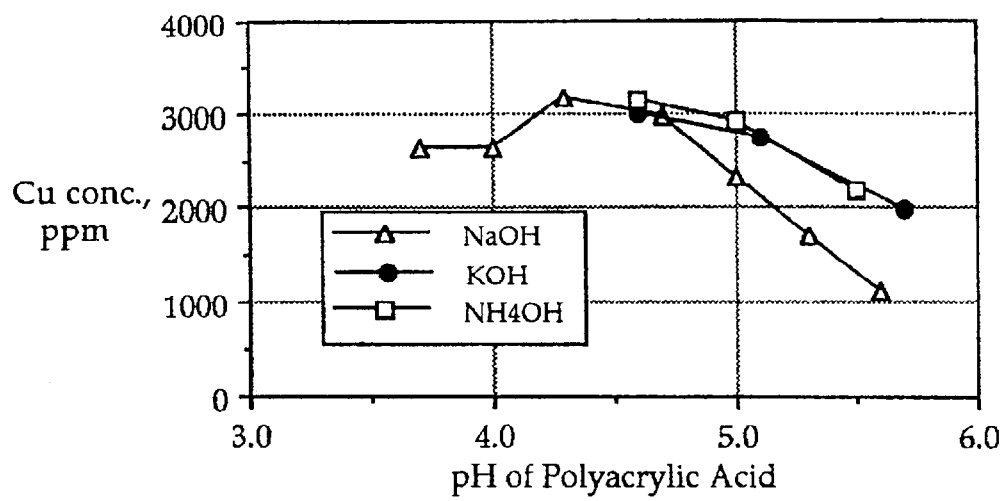
FIG. 5 is a graph of the concentration of copper plotted against the pH of neutralized polyacrylic acid for three different neutralizing agents.

A copper complex solution is prepared according to Example 3 except that the polyacrylic acid is neutralized with three different basic compounds to pHs in the range of 3 to 6. The three basic compounds are sodium hydroxide, potassium hydroxide and ammonium hydroxide. The samples contain 1% by weight polymer solids Goodrite K-752. The different samples are analyzed for copper. The results of the test are shown in FIG. 5 wherein the concentration of copper is graphed against the pH of the neutralized polyacrylic acid for the three different neutralizing compounds.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of controlling bacterial/fungal diseases in plants consisting essentially of the step of applying to said plants a bactericidal/fungicidal amount of a composition consisting essentially of:

an aqueous solution of a complex of copper and between approximately 0.2% by weight and 80% by weight of a partially neutralized, water-soluble polycarboxylic acid having a molecular weight of between approximately 1,000 and 300,000, said aqueous solution having a pH of between approximately 3 and 9, whereby said composition is substantially free of ammonia and is substantially nonphytotoxic to said plant.

2. The method of claim 1, wherein said polycarboxylic acid is selected from the group consisting of polyacrylic acid, polymethacrylic acid, copolymers of acrylic acid and acrylamide, copolymers of acrylic acid and methacrylamide, copolymers of acrylic acid and acrylate esters, copolymers of acrylic acid and methacrylic acid, copolymers of acrylic acid and methacrylate esters, copolymers of acrylic acid and maleic anhydride, carboxymethylcellulose, copolymers of maleic acid and butadiene, polymers of maleic acid and maleic anhydride, copolymers of maleic acid and acrylic acid, and copolymers of methyl vinyl ether and maleic anhydride.

3. The method of claim 1, wherein said molecular weight is between approximately 2,000 and 50,000.

4. The method of claim 1, wherein said pH is between approximately 3.5 and 5.

5. The method of claim 1, wherein said copper is derived from a compound selected from the group consisting of $Cu(OH)_2$, $CuSO_4$, $Cu(ClO_4)_2$, $Cu_2O$, $Cu(NO_3)_2$, $CuCl_2$, copper oxychloride, tribasic copper sulfate, and basic copper carbonate.

6. The method of claim 1, wherein said copper is derived from a compound selected from the group consisting of $Cu(OH)_2$, $Cu_2O$, tribasic copper sulfate, basic copper carbonate and copper oxychloride.

7. The method of claim 1, wherein said copper is present in an amount between approximately 0.1% by weight and 3.2% by weight (copper metal equivalent).

8. The method of claim 1, wherein said polycarboxylic acid is in an amount sufficient to prevent said copper from precipitating.

9. The method of claim 1, wherein said polycarboxylic acid is in an amount between approximately 0.75% and 20% by weight.

10. The method of claim 1, wherein said bacterial plant pathogens are copper tolerant.

11. A method of controlling bacterial/fungal diseases in plants consisting essentially of the step of applying to said plants a bactericide/fungicide consisting essentially of an aqueous solution between approximately 0.1% by weight and 5% by weight (copper metal equivalent) of a complex of copper and between approximately 0.2% by weight and 80% by weight of a partially neutralized, water-soluble polycarboxylic acid having a molecular weight of between approximately 1,000 and 300,000, said aqueous solution having a pH of between approximately 3 and 9, said copper being derived from a substantially water-insoluble copper compound selected from the group consisting of copper hydroxide, cupric oxide, tribasic copper sulfate, basic copper carbonate and copper oxychloride, whereby said bactericide/fungicide is substantially free of ammonia and is substantially nonphytotoxic to said plant.

12. A method of controlling bacterial/fungal diseases in crops consisting essentially of the step of applying to said crops after said crops have been harvested a bactericidal/fungicidal amount of a composition consisting essentially of:
an aqueous solution between approximately 0.1% by weight and 5% by weight (copper metal equivalent) of a complex of copper and between approximately 0.2% by weight and 80% by weight of a partially neutralized, water-soluble polycarboxylic acid having a molecular weight of between approximately 1,000 and 300,000, said aqueous solution having a pH of between approximately 3 and 9, whereby said composition is substantially free of ammonia and is substantially nonphytotoxic to said crops.

13. A method of controlling bacterial/fungal diseases in seed consisting essentially of the step of applying to said seed prior to planting a bactericidal/fungicidal amount of a composition consisting essentially of:
an aqueous solution between approximately 0.1% by weight and 5% by weight (copper metal equivalent) of a complex of copper and between approximately 0.2% by weight and 80% by weight of a partially neutralized, water-soluble polycarboxylic acid having a molecular weight of between approximately 1,000 and 300,000, said aqueous solution having a pH of between approximately 3 and 9, whereby said composition is substantially free of ammonia and is substantially nonphytotoxic to said seed.

14. A method of controlling bacterial/fungal diseases in ornamental plants consisting essentially of the step of applying to the foliage of said ornamental plants a bactericidal/fungicidal amount of a composition consisting essentially of:
an aqueous solution between approximately 0.1% by weight and 5% by weight (copper metal equivalent) of a complex of copper and between approximately 0.2% by weight and 80% by weight of a partially neutralized, water-soluble polycarboxylic acid having a molecular weight of between approximately 1,000 and 300,000, said aqueous solution having a pH of between approximately 3 and 9, whereby said composition is substantially free of ammonia and is substantially nonphytotoxic to said plants.

15. A method of controlling bacterial/fungal diseases in plants consisting essentially of the step of:
applying to said plants a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said solution is substantially nonphytotoxic to said plant.

16. A method of controlling bacterial/fungal diseases in crops consisting essentially of the step of:
applying to said crops after said crops have been harvested a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially nonphytotoxic to said crops.

17. A method of controlling bacterial/fungal diseases in seed consisting essentially of the step of:
applying to said seed prior to planting a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially nonphytotoxic to said seed.

18. A method of controlling bacterial/fungal diseases in ornamental plants consisting essentially of the step of:
applying to the foliage of said ornamental plants a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially nonphytotoxic to said plants.

19. A method of controlling bacterial/fungal diseases in plants consisting essentially of the step of:
applying to said plants a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said solution is substantially free of ammonia and is substantially nonphytotoxic to said plant.

20. A method of controlling bacterial/fungal diseases in crops consisting essentially of the step of:
applying to said crops after said crops have been harvested a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially free of ammonia and is substantially nonphytotoxic to said crops.

21. A method of controlling bacterial/fungal diseases in seed consisting essentially of the step of:
applying to said seed prior to planting a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially free of ammonia and is substantially nonphytotoxic to said seed.

22. A method of controlling bacterial/fungal diseases in ornamental plants consisting essentially of the step of:
applying to the foliage of said ornamental plants a bactericidal/fungicidal amount of a composition consisting essentially of:
an aqueous solution prepared by combining with water a dry composition consisting essentially of a complex of copper and a partially neutralized, water-soluble polycarboxylic acid having a molecular weight of between approximately 1,000 and 300,000, said aqueous solution having a pH of between approximately 3 and 9, and wherein said aqueous solution having between approximately 0.1% by weight and 5% by weight (copper metal equivalent) of complex of copper and between approximately 0.2% by weight and 80% by weight of partially neutralized water-soluble polycarboxylic acid whereby said composition is substantially free of ammonia and is substantially nonphytotoxic to said plants.

* * * * *